United States Patent [19]

Torii et al.

[11] Patent Number: 4,798,890
[45] Date of Patent: Jan. 17, 1989

[54] PROCESS FOR PREPARATION OF AZETIDINONE DERIVATIVES

[75] Inventors: Sigeru Torii; Hideo Tanaka, both of Okayama; Michio Sasaoka; Takashi Shiroi, both of Tokushima, all of Japan

[73] Assignee: Otsuka Kagaku Kabushiki Kaisha, Osaka, Japan

[21] Appl. No.: 186,693

[22] Filed: Apr. 21, 1988

Related U.S. Application Data

[63] Continuation of Ser. No. 680,722, Dec. 12, 1984, abandoned.

[30] Foreign Application Priority Data

May 8, 1984 [JP] Japan ................. 59-92397

[51] Int. Cl.⁴ .............. C07B 45/00; C07D 205.08; C07D 401/06; C07D 403/12
[52] U.S. Cl. ................................. 540/358
[58] Field of Search ......................... 540/358

[56] References Cited

FOREIGN PATENT DOCUMENTS 2261761 9/1975 France .
1503638 3/1978 United Kingdom .

OTHER PUBLICATIONS

Kice I, J.A.C.S., 84, 2384, (1962).
Kice II, J.A.C.S., 86, 2270, (1964).
Lo et al., J.A.C.S., 94, 8253, (1972).
Sheehan J. Organic Chem., 42, 4045, (1977).
Barton/Ollis, Comprehensive Organic Chemistry, vol. 3, (1979), pp. 209, 289, and 301.
Kice, Accounts Chem. Res. 1, (1968), pp. 58–64.
Allan, J. Chem. Soc. Perkin I, (1974), pp. 1456–1459.
Van Leuser, Tetrahedron Letters, 12, (1970), pp. 967–970.
Houben-Weyl, Meth. Org. Chem., vol. 9, (1955), pp. 72–73.
Fugisawa, Chemical Abstracts, vol. 98, No. 23, 6 Jun. 1983, p. 620, abstract No. 197890t.

*Primary Examiner*—Mark L. Berch
*Attorney, Agent, or Firm*—Armstrong, Nikaido, Marmelstein & Kubovcik

[57] ABSTRACT

A process for preparing an azetidinone derivative represented by the formula

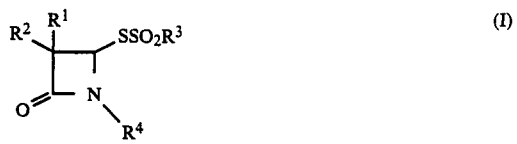

(I)

wherein $R^1$ is hydrogen, halogen or lower alkoxy, $R^2$ is hydrogen, halogen, lower alkoxy, amino or a group

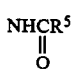

(in which $R^5$ is substituted or unsubstituted phenyl, substituted or unsubstituted phenylmethyl, substituted or unsubstituted phenoxymethyl, or substituted or unsubstituted benzoyl), or $R^1$ and $R^2$, when taken together, are carbonyl, $R^3$ is substituted or unsubstituted phenyl, and $R^4$ is hydrogen, optionally substituted hydrocarbon residue or acyl, silyl, sulfonyl or phosphonyl derived from inorganic acid or organic acid, the process comprising reacting a dithioazetidinone derivative represented by the formula

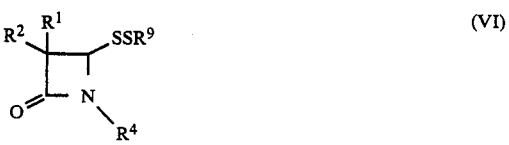

(VI)

wherein $R^1$, $R^2$ and $R^4$ are as defined above and $R^9$ is substituted or unsubstituted, nitrogen-containing aromatic heterocyclic residue with a compound represented by the formula $$R^3SO_2H \qquad (VII)$$

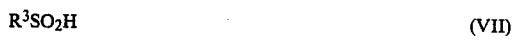

wherein $R^3$ is defined above.

6 Claims, No Drawings

PROCESS FOR PREPARATION OF AZETIDINONE DERIVATIVES

This application is a continuation of application Ser. No. 680,722, filed 12/12/84, now abandoned.

This invention relates to a process for preparing azetidinone derivatives.

The azetidinone derivatives prepared by the process of the present invention are represented by the formula

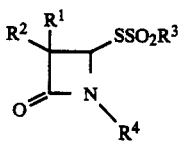

wherein $R^1$ is hydrogen, halogen or lower alkoxy, $R^2$ is hydrogen, halogen, lower alkoxy, amino or a group

(in which $R^5$ is substituted or unsubstituted phenyl, substituted or unsubstituted phenylmethyl, substituted or unsubstituted phenoxymethyl, or substituted or unsubstituted benzoyl), or $R^1$ and $R^2$, when taken together, are carbonyl, $R^3$ is substituted or unsubstituted phenyl, and $R^4$ is hydrogen, optionally substituted hydrocarbon residue or acyl, silyl, sulfonyl or phosphonyl derived from inorganic acid or organic acid.

The azetidinone derivatives of the formula (I) are useful as the intermediates for synthesizing β-lactam antibiotics and can be made into a variety of β-lactam antibiotics depending on the selection of substituents. For example, an azetidinone derivative of the formula (I) wherein $R^4$ is a group

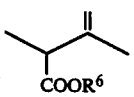

(in which $R^6$ is hydrogen or carboxy protecting group) can be converted into a cephalosporin compound of the formula (III) by the process disclosed in Tetrahedron Letters, 23, 2187 (1982) which is shown in the following reaction scheme.

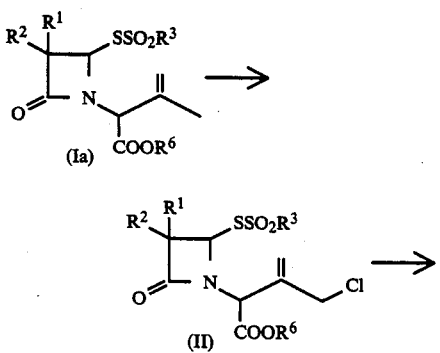

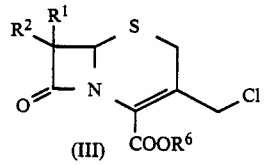

An azetidinone derivative of the formula (I) wherein $R^4$ is hydrogen, silyl, sulfonyl or phosphonyl can be made into various monocyclic β-lactam antibiotics.

Conventional processes for preparing azetidinone derivatives of the formula (I) are described, for example, in Japanese unexamined patent publication (Kokai) No. 129,590/1975. This process comprises, as indicated below by a reaction equation, reacting an azetidinone derivative of the formula (IV) with a heavy metal salt of sulfinic acid of the formula (V) to obtain an azetidinone derivative of the formula (Ib).

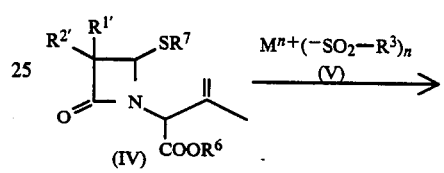

In the foregoing reaction equation, $R^3$ and $R^6$ are as defined above, $R^{1'}$ is hydrogen, $R^{2'}$ is amino or a group $-NHR^8$ (wherein $R^8$ is acyl), $R^7$ is an aromatic hetrocyclic group, aliphatic thioacyl group, aromatic thioacyl group, aromatic aliphatic thioacyl group or alicyclic thioacyl group, M is heavy metal such as copper, silver, mercury, tin or the like and n is the valence of heavy metal. However, the above process, when commercially carried out, involves the disadvantage of using a heavy metal salt of sulfinic acid of the formula (V) which is harmful or expensive.

It is an object of the present invention to provide a commercially advantageous process for preparing the azetidinone derivatives of the formula (I).

It is another object of the invention to provide a process for preparing the azetidinone derivative of the formula (I) without use of a heavy metal salt of sulfinic acid which is harmful or expensive.

It is a further object of the invention to provide a process for preparing the azetidinone derivative of the formula (I) with a high purity and in a high yield by carrying out a simple procedure.

These objects and other features of the present invention will become more apparent from the following description.

According to the present invention, the azetidinone derivative of the formula (I) can be prepared by reacting a dithioazetidinone derivative represented by the formula

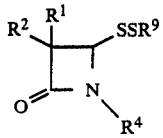 (VI)

wherein $R^1$, $R^2$ and $R^4$ are as defined above and $R^9$ is substituted or unsubstituted, nitrogeno-containing aromatic heterocyclic residue with a compound represented by the formula $$R^3SO_2H \qquad (VII)$$

wherein $R^3$ is as defined above.

Examples of the halogen atoms represented by $R^1$ in the formulae (I) and (VI) are F, Cl, Br, I and the like. Exemplary of the lower alkoxy groups represented by $R^1$ are those having 1 to 4 carbon atoms such as methoxy, ethoxy, propoxy, isopropoxy, butoxy, tert-butoxy, etc.

Examples of the halogen atoms represented by $R^2$ in the formulae (I) and (VI) are F, Cl, Br, I and the like. Illustrative of the lower alkoxy groups represented by $R^2$ are those having 1 to 4 carbon atoms such as methoxy, ethoxy, propoxy, isopropoxy, butoxy and tert-butoxy, etc. Examples of the substituted phenyl groups represented by $R^5$ are phenyl substituted with 1 to 3 $C_1$–$C_4$ alkyl groups such as tolyl; phenyl substituted with 1 to 3 halogen atoms such as 4-chlorophenyl, 2,4-dichlorophenyl, 2,4,6-trichlorophenyl, 4-bromophenyl and 2,4-dibromophenyl; phenyl substituted with 1 to 3 $C_1$–$C_4$ alkoxy group such as 4-methoxyphenyl, 2,4-dimethoxyphenyl and 3,4,5-trimethoxyphenyl; phenyl substituted with 1 to 3 nitro groups such as 4-nitrophenyl and 2,4-dinitrophenyl; etc. Examples of the substituted phenylmethyl groups represented by $R^5$ are phenylmethyl substituted with 1 to 3 $C_1$–$C_4$ alkyl groups on the phenyl ring such as tolylmethyl; phenylmethyl substituted with 1 to 3 halogen atoms on the phenyl ring such as 4-chlorophenylmethyl, 2,4-dichlorophenylmethyl, 2,4,6-trichlorophenylmethyl, 4-bromophenylmethyl and 2,4-dibromophenylmethyl; phenylmethyl substituted with 1 to 3 $C_1$–$C_4$ alkoxy groups on the phenyl ring such as 4-methoxyphenylmethyl, 2,4-dimethoxyphenylmethyl and 3,4,5-trimethoxyphenylmethyl; phenylmethyl substituted with 1 to 3 nitro groups on the phenyl ring such as 4-nitrophenylmethyl and 2,4-dinitrophenylmethyl; phenylmethyl having methylene substituted with halogen, hydroxy, hydroxyimino, $C_1$–$C_4$ alkoxyimino, amino or the like such as phenyldichloromethyl, phenylhydroxymethyl, phenylhydroxyiminomethyl, phenylmethoxyiminomethyl, phenylaminomethyl and phenylacetoxymethyl; etc. Examples of the substituted phenoxymethyl groups represented by $R^5$ are phenoxymethyl substituted with 1 to 3 $C_1$–$C_4$ alkyl groups on the phenyl ring such as tolyloxymethyl; phenoxymethylsubstituted with 1 to 3 halogen atoms on the phenyl ring such as 4-chlorophenoxymethyl, 2,4-dichlorophenoxymethyl, 2,4,6-trichlorophenoxymethyl, 4-bromophenoxymethyl and 2,4-dibromophenoxymethyl; phenoxymethyl substituted with 1 to 3 $C_1$–$C_4$ alkoxy groups on the phenyl ring such as 4-methoxyphenoxymethyl, 2,4-dimethoxyphenoxymethyl and 3,4,5-trimethoxyphenoxymethyl; phenoxymethyl substituted with 1 to 3 nitro groups on the phenyl ring such as 4-nitrophenoxymethyl and 2,4-dinitrophenoxymethyl; etc. Examples of the substituted benzoyl groups represented by $R^5$ are benzoyl substituted with 1 to 3 $C_1$–$C_4$ alkyl groups on the phenyl ring such as toluoyl; benzoyl substituted with 1 to 3 halogen atoms on the phenyl ring such as 4-chlorobenzoyl, 2,4-dichlorobenzoyl, 2,4,6-trichlorobenzoyl, 4-bromobenzoyl and 2,4-dibromobenzoyl; benzoyl substituted with 1 to 3 $C_1$–$C_4$ alkoxy groups on the phenyl ring such as 4-methoxybenzoyl, 2,4-dimethoxybenzoyl and 3,4,5-trimethoxybenzoyl; benzoyl substituted with 1 to 3 nitro groups on the phenyl ring such as 4-nitrobenzoyl and 2,4-dinitrobenzoyl; etc.

Examples of the substituted phenyl represented by $R^3$ in the formulae (I) and (VII) are phenyl substituted with 1 to 3 $C_1$–$C_4$ alkyl groups such as tolyl and xylyl; phenyl substituted with 1 to 3 halogen atoms such as 4-chlorophenyl, 2,4-dichlorophenyl, 2,4,6-trichlorophenyl, 4-bromophenyl and 2,4-dibromophenyl; phenyl substituted with 1 to 3 $C_1$–$C_4$ alkoxy groups such as 4-methoxyphenyl, 2,4-dimethoxyphenyl and 3,4,5-trimethoxyphenyl; phenyl substituted with 1 to 3 nitro groups such as 4-nitrophenyl and 2,4-dinitrophenyl; etc.

The groups represented by $R^4$ in the formulae (I) and (VI) are hydrogen, acyl, silyl, sulfonyl and phosphonyl derived from inorganic or organic acid, and optionally substituted hydrocarbon residue. Of these groups, the optionally substituted hydrocarbon residue is preferred. Exemplary of the substituted hydrocarbon residue are groups

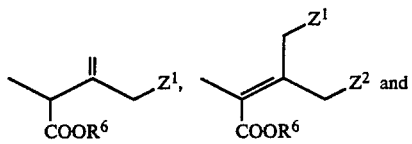

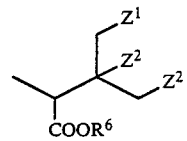

wherein $R^6$ is hydrogen or carboxy protecting group. The wide range of carboxy protecting groups as disclosed in Theodora W. Greene: "Protective Groups in Organic Synthesis," Chapter 5 are usable in the present invention. Typical examples of the groups are phenyl $C_1$–$C_4$ alkyl optionally having 1 to 3 substituents, e.g., $C_1$–$C_4$ alkoxy, halogen, methylenedioxy, $C_1$–$C_4$ alkyl or nitro on the phenyl ring such as benzyl, p-methoxybenzyl, trimethoxybenzyl, trimethoxydichlorobenzyl, piperonyl, diphenylmethyl, bis(p-methoxyphenyl)methyl, ditolylmethyl, phenyl-p-methoxyphenylmethyl, α-p-methoxyphenylmethyl, trityl, α-diphenylethyl, p-nitrobenzyl, o-nitrobenzyl and o,p-dinitrobenzyl; $C_1$–$C_4$ alkyl which may have at least one substituent selected from halogen, phenyl substituted with 1 to 3 $C_1$–$C_4$ alkoxy groups, benzoyl, benzoyl substituted with 1 to 3 halogen atoms on the phenyl ring, $C_1$–$C_4$ alkoxy, $C_1$–$C_4$ alkoxy substituted with 1 to 3 $C_1$–$C_4$ alkoxy groups, benzyloxy, $C_1$–$C_4$ alkanoyl and $C_1$–$C_4$ alkoxycarbonyl, such as tert-butyl, trichloroethyl, α-p-methoxyphenyl-β-trichloroethyl, phenacyl, p-bromophenacyl, methoxymethyl, isopropoxymethyl, methoxyethoxymethyl, benzyloxymethyl and 1-methoxycarbonyl-2-oxopropyl; cumyl; fluorenyl; etc. $Z^1$ and $Z^2$ are the same or different and are each hydrogen, halogen, sulfur-containing group, oxygen-containing group, nitrogen-containing group or the like. Examples of the substituents represented by $Z^1$ and $Z^2$ are halogen such as bromine, chlorine and fluorine; sulfur-containing groups, e.g., $C_1$–$C_4$ alkylthio such as methylthio and ethylthio, phenylthio optionally substituted with 1 to 5 nitro groups or halogen atoms on the phenyl ring such as phenylthio, p-nitrophenylthio and pentachlorophenylthio, 2-pyridylthio, 2-benzothiadiazolylthio, 1,3,4-thiadiazol-5-ylthio, 2-substituted-1,3,4-thiadiazol-5-ylthio, 1,2,3,4-tetrazol-5-ylthio, 1-substituted-1,2,3,4-tetrazol-5-ylthio, O-ethyldithiocarbonate, N,N-diethyldithiocarbamate, phenylsulfonyl and p-methylphenylsulfonyl; oxygen-containing groups, e.g., hydroxy, $C_1$–$C_4$ alkoxy such as methoxy and ethoxy, $C_1$–$C_4$ acyloxy such as acetoxy, benzoyloxy, nitrosoxy, nitriloxy, diphenylphosphonyloxy, methanesulfonate, N-morphonyl and diphenylmethyloxy; nitrogen-containing groups, e.g., di($C_1$–$C_4$ alkyl)amino such as dimethylamino, and piperidin-1-yl; etc.

Examples of the substituted or unsubstituted nitrogen-containing aromatic heterocyclic residue represented by $R^9$ in the formula (VI) are those optionally having 1 to 3 substituents, e.g., with $C_1$–$C_4$ alkyl, phenyl, $C_1$–$C_4$ alkoxy, nitro or halogen, such as thiazol-2-yl, 4-methylthiazol-2-yl, 5-methylthiazol-2-yl, 4-phenylthiazol-2-yl, 5-phenylthiazol-2-yl, thiadiazol-2-yl, 5-methylthiadiazol-2-yl, 5-phenylthiadiazol-2-yl, 5-methoxycarbonylthiadiazol-2-yl, benzothiazol-2-yl, 4-methylbenzothiazol-2-yl, 6-methylbenzothiazol-2-yl, 5-methoxybenzothiazol-2-yl, 6-nitrobenzothiazol-2-yl, 5-chlorobenzothiazol-2-yl, benzoxazol-2-yl, 4-methylbenzoxazol-2-yl, 6-phenylbenzoxazol-2-yl, 5-methoxybenzoxazol-2-yl, 5-chlorobenzoxazol-2-yl, benzimidazol-2-yl, 5-methylbenzimidazol-2-yl, 6-chlorobenzoimidazol-2-yl, pyrimidin-2-yl, 5-methylpyrimidin-2-yl and 2-pyridyl, etc.

The dithioazetidinone derivatives of the formula (VI) used as one of the starting materials in the present invention are known and can be synthesized by various processes. The synthesizing processes using penicillin are disclosed, for example, in Tetrahedron Letters, 3001 (1973), J. Amer. Chem. Soc., 86, 5307 (1964): Japanese examined patent publication (Kokoku) No. 14665/1981; Japanese unexamined patent publications (Kokai) Nos. 29587/1982, 59896/1982, 183793/1982 and 183794/1982; and The Collection of Drafted Research Reports for the 9th International Convention on Heterocycle, page 300 (1983). The derivatives of the formula (VI) can be produced also by a combination of processes described in these publications. These known processes are shown, for example, in the following reaction scheme.

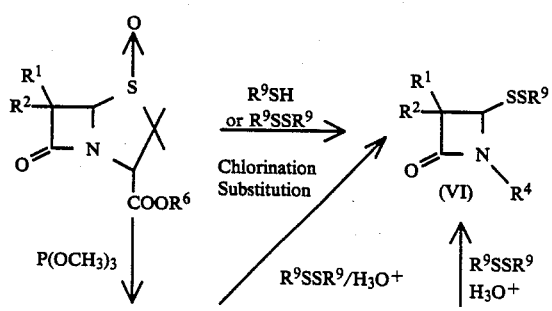

-continued

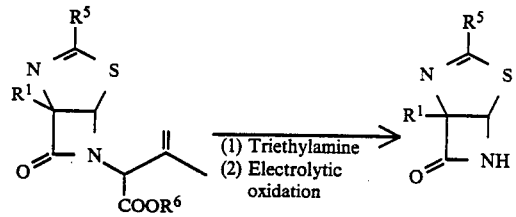

In the above reaction scheme, $R^1$, $R^2$, $R^4$, $R^5$, $R^6$ and $R^9$ are as defined above.

However, the dithioazetidinone derivatives of the formula (VI) as used in the present invention are not limited to those producible by these processes. An extensive range of dithioazetidinone derivatives of the formula (VI) produced by various processes including those other than the foregoing processes can be used as the starting material in the present invention.

The compounds of the formula (VII), namely the other starting material used in the present invention, are also known. Examples of the compound of the formula (VII) as used are benzenesulfinic acid, tolylsulfinic acid, xylylsulfinic acid, 4-chlorophenylsulfinic acid, 2,4-dichlorophenylsulfinic acid, 2,4,6-trichlorophenylsulfinic acid, 4-bromophenylsulfinic acid, 2,4-dibromophenylsulfinic acid, 4-methoxyphenylsulfinic acid, 2,4-dimethoxyphenylsulfinic acid, 3,4,5-trimethoxyphenylsulfinic acid, 4-nitrophenylsulfinic acid, 2,4-dinitrophenylsulfinic acid, etc.

According to the present invention, the dithioazetidinone derivative of the formula (VI) is reacted with the compound of the formula (VII) usually in a suitable solvent. Examples of the solvent which can be used in the present invention is not particularly limited as far as the solvent is capable of dissolving the compound of the formula (VI) and the compound of the formula (VII). Since these compounds need not be completely dissolved in the present invention, even solvents capable of partially dissolving them are unable. Useful solvents include organic solvents used singly or in conjunction with water. Examples of suitable organic solvents are ketones such as acetone, methyl ethyl ketone, diethyl ketone and methyl isobutyl ketone; esters such as methyl formate, ethyl formate, propyl formate, methyl acetate, ethyl acetate, propyl acetate, methyl propionate and ethyl propionate; aromatic hydrocarbons such as benzene, toluene and xylene; halogenated hydrocarbons such as dichloromethane, dibromomethane, chloroform, bromoform, carbon tetrachloride, dichloroethane, dibromoethane and trichloroethane; ethers such as diethyl ether, dipropyl ether, dibutyl ether, tetrahydrofuran and dioxane; nitroalkanes such as nitromethane, nitroethane and nitropropane; nitriles such as acetonitrile, propionitrile, butyronitrile and valeronitrile; alcohols such as methanol, ethanol, propanol, isopropanol and butanol; etc. These organic solvents can be used singly or at least two of them are usable in admixture. The amount of the solvent is usually about 1 to about 400 times, preferably about 1 to about 100 times, more preferably about 1 to about 50 times, the weight of the compound of the formula (VI).

The proportions of the compounds of the formulae (VI) and (VII) used in the present invention are not particularly limited and can be suitably determined over a wide range. Usually about 1 to about 5 moles, preferably about 1 to about 2 moles, more preferably about 1 to about 1.5 moles, of the compound of the formula (VII) is used per mole of the compound of the formula (VI).

The reaction of the present invention can be usually carried out at a temperature ranging from about −20° C. to the temperature at which the solvent used is refluxed. Preferred reaction temperature is in the range of 0° to about 50° C. The reaction time in the present invention varies depending on the reaction temperature, kinds of the compounds (VI) and (VII) and the other conditions, but ususally ranges from about 0.1 to about 15 hours.

After the completion of the reaction, the azetidinone derivative (I) of the present invention can be separated from the reaction mixture by conventional methods such as filtration, centrifugation, distillation, extraction, etc. The azetidinone derivative (I) thus obtained is substantially pure, but can be easily purified by recrystallization, column chromatography or like means if further purification is needed.

According to the present invention, a desired compound (I) of high purity can be prepared in high yields without use of expensive or harmful heavy metal salt of sulfinic acid by carrying out a simple procedure.

The present invention will be described below in more detail with reference to the following Examples to which, however, the present invention is limited in no way and in which the code Ph refers to phenyl.

EXAMPLE 1

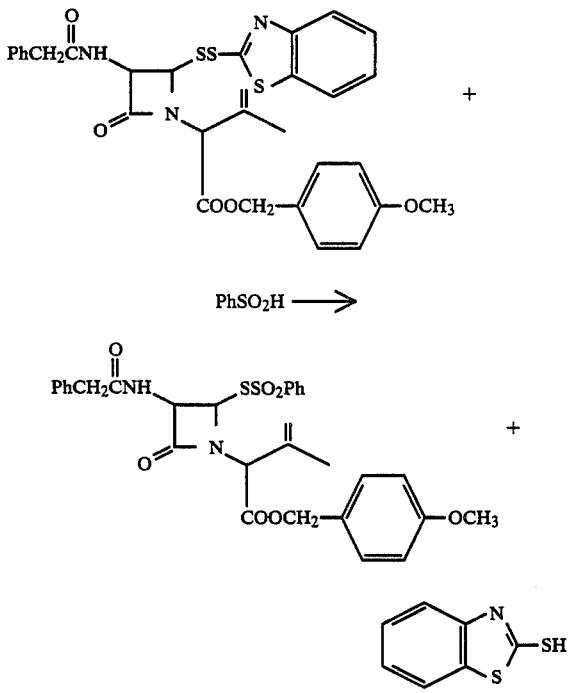

Dissolved in 10 ml of acetone was 1.0 g of p-methoxybenzyl 2-[3-phenylacetamido-4-(2-benzothiazolyldithio)-2-azetidinon-1-yl]-3-methyl-3-butenoate. To the solution was added 0.28 g of benzenesulfinic acid and the mixture was reacted with stirring at room temperature for 4 hours. The acetone was distilled off under reduced pressure and the resulting residue was purified by silica gel column chromatography, giving p-methoxybenzyl 2-(3-phenylacetamido-4-benzenesulfonylthio-2-azetidinon-1-yl)-3-methyl-3-butenoate in a yield of 97%. The NMR spectrum data of the compound thus obtained were identical with those of the desired compound. Table 3 shows the NMR spectrum data of the compound.

EXAMPLE 2 p-Methoxybenzyl2-[3-phenylacetamido-4-(2-benzothiazolyldithio)-2-azetidinon-1-yl]-3-methyl-3-butenoate was reacted in the same manner as in Example 1 by using the solvents as shown below in Table 1, producing p-methoxybenzyl-2-(3-phenylacetamido-4-benzenesulfonylthio-2-azetidinon-1-yl)-3-methyl-3-butenoate in the yields listed below in Table 1. The NMR spectrum data of the compounds thus obtained were identical with those of the compound produced in Example 1.

TABLE 1

| Solvent | Yield (%) |
|---|---|
| Acetone-water (20:1) | 95 |
| Acetonitrile | 93 |
| Tetrahydrofuran | 98 |
| Dioxane | 90 |

EXAMPLE 3

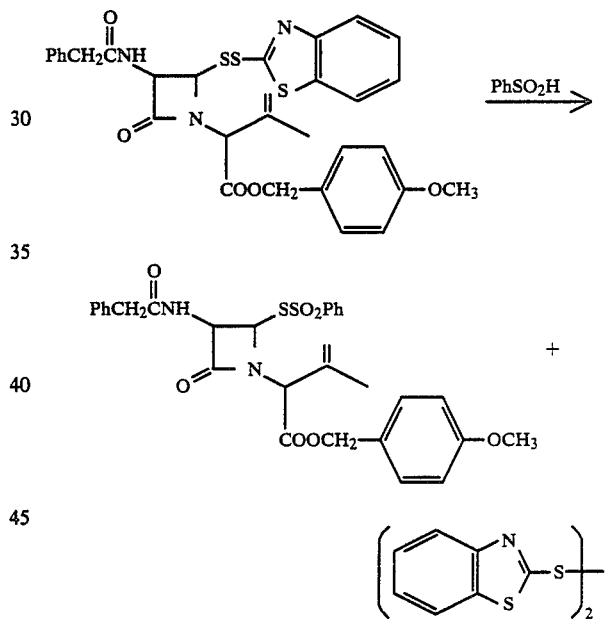

A 10 g quantity of p-methoxybenzyl 2-[3-phenylacetamido-4-(2-benzothiazolyldithio)-2-azetidinon-1-yl]-3-methyl-3-butenoate was dissolved in 100 ml of acetone. To the solution was added 2.8 g of benzenesulfinic acid, and the mixture was reacted with stirring at room temperature for 4 hours. The reaction mixture was mixed with 0.91 g of a 30% aqueous solution of hydrogen peroxide and the resulting mixture was reacted with stirring at room temperature for 1 hour. The precipitated 2-benzothiazolyl disulfide was filtered and the acetone was removed from the filtrate under reduced pressure by distillation. The residue was dissolved in benzene and the solution was washed sequentially with an aqueous $Na_2S_2O_3$ solution and with water and dried over anhydrous sodium sulfate. The benzene was distilled off under reduced pressure to give p-methoxybenzyl 2-(3-phenylacetamido-4-benzenesulfonylthio-2-azetidinon-1-yl)-2-methyl-3-butenoate. The compound thus obtained was purified by recrystallization from benzene (yield 92%). The NMR spectrum data of the compound were identical with those of the compound produced in Example 1.

EXAMPLE 4

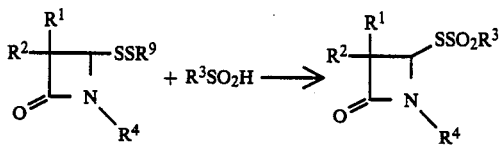

The compounds shown below in Table 2 were produced by following the general procedure of Example 1. The NMR spectrum data of these compounds were identical with those of the compounds as contemplated, Table 3 below lists the spectral data thereof.

TABLE 2

| $R^1$ | $R^2$ | $R^9$ | $R^4$ | $R^3$ | Yield (%) |
|---|---|---|---|---|---|
| H | PhOCH₂C(O)NH— | 5-methoxy-benzothiazol-2-yl | CH₂=C(CH₃)—CH(COOCH₂Ph)— | Ph | 90 |
| H | PhOCH₂C(O)NH— | 5-methyl-1,3,4-thiadiazol-2-yl | CH₂=C(CH₃)—CH(COOCH₂Ph)— | Ph | 92 |
| H | PhCH₂C(O)NH— | benzothiazol-2-yl | CH₂=C(CH₃)—CH(COOCH₃)— | p-tolyl (CH₃-C₆H₄-) | 98 |
| H | PhOCH₂C(O)NH— | benzothiazol-2-yl | CH₂=C(CH₃)—CH(COOCH₂-3,4,5-(OCH₃)₃-C₆H₂)— | Ph | 91 |
| H | PhOCH₂CNH | benzothiazol-2-yl | CH₂=C(CH₃)—CH(COOCH₂-4-OCH₃-C₆H₄)— | Ph | 94 |
| H | PhOCH₂CNH | 6-nitro-benzothiazol-2-yl | CH₂=C(CH₃)—CH(COOCH₂Ph)— | Ph | 90 |
| H | PhOCH₂CNH | 4-methyl-benzothiazol-2-yl | CH₂=C(CH₃)—CH(COOCH₂-2,5-diCl-3,4,6-(OCH₃)₃-C₆)— | Ph | 94 |

TABLE 2-continued

| R¹ | R² | R⁹ | R⁴ | R³ | Yield (%) |
|---|---|---|---|---|---|
| H | PhOCH₂C(O)NH | 2-methyl-6-methylbenzothiazole | CH₂=C(CH₃)CH(CH₃)COOCH₂C₆H₄-4-Br | Ph | 91 |
| H | PhOCH₂C(O)NH— | 2-methylbenzothiazole | CH₂=C(CH₃)CH(CH₃)COO-(9-fluorenyl) | Ph | 90 |
| H | PhCH₂C(O)NH— | 2-methylbenzothiazole | CH₂=C(CH₃)CH(CH₃)COO-(9-fluorenyl) | Ph | 92 |
| H | PhCH₂C(O)NH— | 2-methylbenzothiazole | CH₂=C(CH₃)CH(CH₃)COOCH₂C₆H₄-4-NO₂ | Ph | 98 |
| H | PhCH₂C(O)NH— | 2-methylbenzothiazole | CH₂=C(CH₃)CH(CH₃)COOCH₂C₆H₄-2-NO₂ | Ph | 90 |
| H | PhOCH₂C(O)NH— | 2-methylbenzothiazole | CH₂=C(CH₃)CH(CH₃)COOCH(COCH₃)(CO₂CH₃) | Ph | 95 |
| H | PhCH₂C(O)NH— | 2-methylbenzothiazole | CH₂=C(CH₃)CH(CH₃)COOCH₃ | 4-Cl-C₆H₄ | 90 |
| H | PhCH₂C(O)NH— | 2-methylbenzothiazole | CH₂=C(CH₃)CH(CH₃)COOCH₃ | 4-NO₂-C₆H₄ | 91 |

TABLE 2-continued

| R¹ | R² | R⁹ | R⁴ | R³ | Yield (%) |
|---|---|---|---|---|---|
| H | PhCH₂C(O)NH— | 2-benzothiazolyl | CH₂=C(CH₃)–CH(COOCH₂Ph)– | 4-NO₂–C₆H₄– | 92 |
| H | PhCH₂C(O)NH— | 2-benzothiazolyl | CH₂=C(CH₃)–CH(COOCH₂Ph)– | 4-CH₃O–C₆H₄– | 91 |
| CH₃O— | PhCH₂C(O)NH— | 2-benzothiazolyl | CH₂=C(CH₃)–CH(COOCH₂-C₆H₄-4-NO₂)– | Ph | 94 |
| CH₃O— | PhCH₂C(O)NH— | 2-pyridyl | CH₂=C(CH₃)–CH(COOCH₂-C₆H₄-4-NO₂)– | Ph | 94 |
| H | PhCH₂C(O)NH— | 2-pyridyl | CH₂=C(CH₃)–CH(COOCH₂-C₆H₄-4-OCH₃)– | Ph | 92 |
| H | PhCH₂C(O)NH— | 2-benzothiazolyl | (CH₃)(CH₃)C=C(COOCH₂CCl₃)– | 4-CH₃–C₆H₄– | 93 |
| H | PhCH₂C(O)NH— | 2-benzothiazolyl | (CH₃)(CH₃)C=C(COOCH₂CCl₃)– | 4-CH₃O–C₆H₄– | 96 |

TABLE 3

Structure:

$$\begin{array}{c} R^2\ R^1\quad SSO_2R^3 \\ \diagdown\ |\ / \\ \text{β-lactam ring with } N-R^4 \end{array}$$

| R¹ | R² | R⁴ | R³ | NMR(CDCl₃, δ, J=Hz) |
|---|---|---|---|---|
| H | PhCH₂C(O)NH— | CH₂=C(CH₃)–CH(COOCH₂-C₆H₄-4-OCH₃)– | Ph | 1.71(s, 3H), 3.54(s, 2H), 3.78(s, 3H), 4.45(s, 1H), 4.69(s, 1H), 4.72(bs, 1H), 5.02(s, 1H), 5.06(dd, 1H, J=4.0 and 6.5), 5.70(d, 1H, J=4.0), 5.90(d, 1H, J=6.5), 6.82(d, 2H, J=7.0), 7.00–7.85(m, 12H) |

TABLE 3-continued

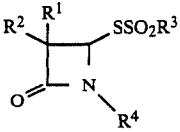

| R¹ | R² | R⁴ | R³ | NMR(CDCl₃, δ, J=Hz) |
|---|---|---|---|---|
| H | PhOCH₂C(O)NH— | CH₂=C(CH₃)–CH(COOCH₂Ph)– | Ph | 1.78(s, 3H), 4.37 and 4.42(ABq, 2H, J=12.0), 4.55(s, 1H), 4.79(s, 1H), 4.82(bs, 1H), 5.14(s, 2H), 5.27(dd, 1H, J=4.0 and 7.0), 5.87(d, 1H, J=4.0), 6.75–7.90(m, 16H) |
| " | PhCH₂C(O)NH— | CH₂=C(CH₃)–CH(COOCH₃)– | p-tolyl | 1.74(s, 3H), 2.40(s, 3H), 3.50(s, 2H), 3.71(s, 3H), 4.64(s, 1H), 4.70(s, 1H), 4.89(s, 1H), 5.05(dd, 1H, J=5 and 8), 5.78(d, 1H, J=5), 6.52(d, H, J=8), 7.22(s, 5H), 7.30(d, 2H, J=9), 7.68(d, 2H, J=9) |
| H | PhOCH₂C(O)NH— | CH₂=C(CH₃)–CH(COOCH₂–3,4,5-(OCH₃)₃C₆H₂)– | " | 1.79(s, 3H), 3.85(s, 9H), 4.35 and 4.41 (ABq, 2H, J=12.5), 4.62(s, 1H), 4.80(s, 1H), 4.84(bs, 1H), 5.08(s, 2H), 5.26(dd, 1H, J=4 and 7), 5.84 (d, 1H, J=4), 6.54(s, 2H), 6.75–7.90(m, 11H) |
| " | " | CH₂=C(CH₃)–CH(COOCH₂–4-OCH₃C₆H₄)– | " | 1.76(s, 3H), 3.77(s, 3H), 4.34 and 4.40 (ABq, 2H, J=12), 4.53(s, 1H), 4.76(s, 1H), 4.79(bs, 1H), 5.07(s, 2H), 5.27(dd, 1H, J=4 and 6.5), 5.86(d, 1H, J=4), 6.65–7.90(m, 15H) |
| H | PhOCH₂C(O)NH— | CH₂=C(CH₃)–CH(COOCH₂–2,6-Cl₂-3,4,5-(OCH₃)₃C₆)– | Ph | 1.76(s, 3H), 3.89(s, 6H), 3.94(s, 3H), 4.36 and 4.41(ABq, 2H, J=12), 4.60(s, 1H), 4.78(bs, 1H), 4.80(s, 1H), 5.24(dd, 1H, J=4 and 6.5), 5.38 (s, 2H), 5.88(s, 2H), 6.75–7.90(m, 11H) |
| " | " | CH₂=C(CH₃)–CH(COOCH₂C(O)–4-BrC₆H₄)– | " | 1.85(s, 3H), 4.38 and 4.44(ABq, 2H, J=12), 4.90(s, 1H), 4.96(s, 2H), 5.28 and 5.34 (ABq, 2H, J=12), 5.35(dd, 1H, J=4 and 6.5), 5.85(d, 1H, J= 4), 6.75–7.95(m, 15H) |

TABLE 3-continued $$\begin{array}{c} R^2 \phantom{x} R^1 \phantom{xx} SSO_2R^3 \\ \diagdown \phantom{xx} \diagup \\ \text{(β-lactam ring)} \\ N-R^4 \end{array}$$

| R¹ | R² | R⁴ | R³ | NMR(CDCl₃, δ, J=Hz) |
|---|---|---|---|---|
| H | PhOCH₂C(O)NH— | CH₂=C(CH₃)–CH(CH₃)–...–COO–CH(fluorenyl) | Ph | 1.78(s, 3H), 4.39 and 4.44(ABq, 2H, J=12), 4.76(s, 1H), 4.85(s, 1H), 4.88(bs, 1H), 5.34(dd, 1H, J=4.7 and 8.2), 5.87(d, 1H, J=4.7), 6.76(s, 1H), 6.80–7.90(m, 19H) |
| " | PhCH₂C(O)NH— | " | " | 1.76(s, 3H), 3.57(s, 2H), 4.71(s, 1H), 4.82(s, 1H), 4.84(s, 1H), 5.16(dd, 1H, J=4.7 and 8.1), 5.76(d, 1H, J=4.7), 6.50(d, 1H, J=8.1), 6.74(s, 1H), 7.05–7.90(m, 18H) |
| H | PhCH₂C(O)NH— | CH₂=C(CH₃)–CH(CH₃)–COOCH₂–C₆H₄–NO₂ (para) | Ph | 1.78(s, 3H), 3.56(s, 2H), 4.57(s, 1H), 4.76(s, 1H), 4.88(bs, 1H), 5.11(dd, 1H, J=4 and 7), 5.23(s, 2H), 5.72(d, 1H, J=4), 6.06(d, 1H, J=7), 7.00–8.00(m, 12H), 8.19(d, 2H, J=7) |
| " | " | CH₂=C(CH₃)–CH(CH₃)–COOCH₂–C₆H₄–NO₂ (ortho) | " | 1.78(s, 3H), 3.56(s, 2H), 4.60(s, 1H), 4.76(s, 1H), 4.87(bs, 1H), 5.12(dd, 1H, J=4 and 6.5), 5.53(s, 2H), 5.64(d, 1H, J=4), 6.20(d, 1H, J=6.5), 7.10–8.20(m, 14H) |
| H | PhOCH₂C(O)NH— | CH₂=C(CH₃)–CH(CH₃)–COOCH(COCH₃)–CO₂CH₃ | Ph | 1.84(s, 3H), 2.35(s, 3H), 3.83(s, 3H), 4.38 and 4.45(ABq, 2H, J=11), 4.80–5.05(m, 3H), 5.38(dd, 1H, J=4 and 7), 5.55(s, 1H), 5.85(d, 1H, J=4.0), 6.75–8.00(m, 11H) |
| " | PhCH₂C(O)NH— | CH₂=C(CH₃)–CH(CH₃)–COOCH₃ | 4-Cl–C₆H₄– | 1.78(s, 3H), 3.51(bs, 2H), 3.70(s, 3H), 4.61(bs, 1H), 4.76(s, 1H), 4.86(bs, 1H), 5.06(dd, 1H, J=5 and 8), 5.83(d, 1H, J=5), 7.14(d, 1H, J=8), 7.23(s, 5H), 7.43(d, 2H, J=8), 7.81(d, 2H, J=8) |

TABLE 3-continued

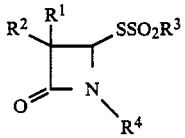

| R¹ | R² | R⁴ | R³ | NMR(CDCl₃, δ, J=Hz) |
|---|---|---|---|---|
| H | PhCH₂C(O)NH— | CH₂=C(CH₃)–, COOCH₂Ph (isopropylidene) | –C₆H₄–NO₂ (p) | 1.75(s, 3H), 3.50(s, 2H), 4.76(bs, 1H), 4.84(s, 1H), 4.92(bs, 1H), 5.10(dd, 1H, J=5 and 8), 5.12(s, 2H), 5.92(d, 1H, J=5), 6.91(d, 1H, J=8), 7.20(s, 5H), 7.30(s, 5H), 7.87(d, 2H, J=9), 8.18(d, 2H, J=9) |
| ″ | ″ | ″ | –C₆H₄–OCH₃ (p) | 1.75(s, 3H), 3.50(s, 2H), 3.79(s, 3H), 4.65 (bs, 1H), 4.77(s, 1H), 4.85(bs, 1H), 5.12(dd, 1H, J=5 and 8), 5.13 (s, 2H), 5.73(d, 1H, J=5), 6.63(d, 1H, J=8), 6.87(d, 2H, J=9), 7.20(s, 5H), 7.29(s, 5H), 7.67(d, 2H, J=9) |
| H | PhCH₂C(O)NH— | CH₂=C(CH₃)–, COOCH₃ | –C₆H₄–NO₂ (p) | 1.80(s, 3H), 3.52(bs, 2H), 3.70(s, 3H), 4.55 (bs, 1H), 4.79(s, 1H), 4.87(bs, 1H), 5.03(dd, 1H, J=5 and 8), 5.87 (d, 1H, J=5), 6.73(d, 1H, J=8), 7.22(s, 5H), 7.94(d, 2H, J=9), 8.24(d, 2H, J=9) |
| CH₃O— | ″ | CH₂=C(CH₃)–, COOCH₂–C₆H₄–NO₂ | Ph | 1.79(s, 3H), 3.46(s, 3H), 3.61(s, 2H), 4.57(s, 1H), 4.81(s, 1H), 4.88(bs, 1H), 5.23(s, 2H), 5.29(s, 1H), 6.00(bs, 1H), 7.10–7.90(m, 12H), 8.17(d, 2H, J=9) |
| H | PhCH₂C(O)NH— | (CH₃)C=C(CH₃)–COOCH₂CCl₃ | –C₆H₄–CH₃ (p) | 1.91(s, 3H), 2.15(s, 3H), 3.60(s, 2H), 4.60–4.80(m, 3H), 5.83(d, 1H, J=5Hz), 7.20(m, 8H), 7.66(d, 2H, J=9Hz) |
| ″ | ″ | ″ | –C₆H₄–OCH₃ (p) | 1.90(s, 3H), 2.13(s, 3H), 3.50(s, 2H), 3.75(s, 3H), 4.60–4.80(m, 3H), 5.85(d, 1H, J=4.5Hz), 6.84(d, 2H, J=7Hz), 7.20(m, 6H), 7.77 (d, 2H, J=7Hz) |

We claim:

1. A process for preparing an azetidinone derivative represented by the formula

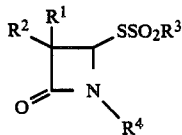
(I)

wherein R¹ is hydrogen, halogen or lower alkoxy, R² is hydrogen, a halogen, lower alkoxy, amino or a group $$\text{NHCR}^5 \atop \text{\|} \atop \text{O}$$

(in which R⁵ is substituted or unsubstituted phenyl, substituted or unsubstituted phenylmethyl, substituted or unsubstituted phenoxymethyl, or substituted or unsubstituted benzoyl), or R¹ and R², when taken together with the carbon atom in the azetidinone ring, are carbonyl, R³ is substituted or unsubstituted phenyl, and R⁴ is hydrogen or one of the following groups

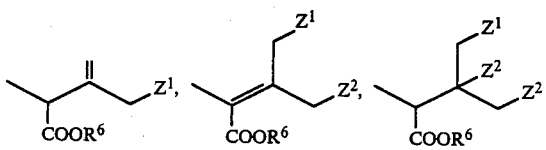

(in which $R^6$ is hydrogen or a carboxy protecting group, and $Z^1$ and $Z^2$ are the same or different and represent hydrogen, a halogen, $C_1$–$C_4$ alkylthio, phenylthio optionally substituted with 1 to 5 nitro groups or halogen atoms on the phenyl ring, 2-pyridylthio, 2-benzothiadiazolylthio, 1,3,4-thiadiazol-5-ylthio, 1,2,3,4-tetrazol-4-ylthio, O-ethyldithiocarbonate, N,N-diethyldithiocarbamate, phenyl-sulfonyl, p-methylphenylsulfonyl, hydroxy, $C_1$–$C_4$ alkoxy, $C_1$–$C_4$ acyloxy, benzoyloxy, nitrosoxy, diphenylphosphonyloxy, methanesulfonate, diphenylmethyloxy, di($C_1$–$C_4$ alkyl)amino or piperidin-1-yl), the process consisting essentially of reacting a dithioazetidinone derivative represented by the formula

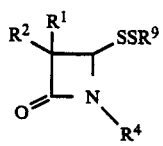 (VI)

wherein $R^1$, $R^2$ and $R^4$ are as defined above and $R^9$ is a substituted or unsubstituted nitrogen-containing aromatic heterocyclic residue with a compound represented by the formula $R^3SO_2H$ (VII)

wherein $R^3$ is as defined above, said reaction being conducted in a reaction system consisting essentially of the dithioazetidinone derivative of formula (VI), the compound of formula (VII), and an organic solvent or a mixture of said organic solvent and water, the organic solvent being at least one selected from the group consisting of ketones, esters, aromatic hydrocarbons, halogenated hydrocarbons, ethers, nitroalkanes, nitriles and alcohols.

2. A process as defined in claim 1 in which $R^1$ in the dithioazetidinone derivative of the formula (VI) is hydrogen, F, Cl, Br, I or $C_1$–$C_4$ alkoxy, $R^2$ is hydrogen, F, Cl, Br, I, $C_1$–$C_4$ alkoxy, amino or a group

in which $R^5$ is phenyl; phenyl having 1 to 3 substituents on the phenyl ring selected from $C_1$–$C_4$ alkyl, F, Cl, Br, I, $C_1$–$C_4$ alkoxy and nitro; phenylmethyl; phenylmethyl having 1 to 3 substituents on the phenyl ring selected from $C_1$–$C_4$ alkyl, F, Cl, Br, I, $C_1$–$C_4$ alkoxy and nitro; phenylmethyl having methylene substituted with halogen, hydroxy, hydroximino, $C_1$–$C_4$ alkoxyimino or amino; phenoxymethyl; phenoxymethyl having 1 to 3 substituents on the phenyl ring selected from $C_1$–$C_4$ alkyl, F, Cl, Br, I, $C_1$–$C_4$ alkoxy and nitro; benzoyl; or benzoyl having 1 to 3 substituents on the phenyl ring selected from $C_1$–$C_4$ alkyl, F, Cl, Br, I, $C_1$–$C_4$ alkoxy and nitro), or $R^1$ or $R^2$ are carbonyl when taken together with the carbon atom in the azetidinone ring, $R^4$ is as defined in claim 1

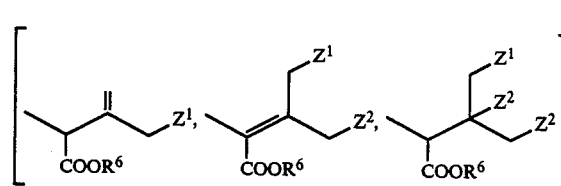

and $R^9$ is said heterocyclic residue selected from the group consisting of thiazol-2-yl, thiadiazol-2-yl, benzothiaziol-2-yl, benzoxazol-2-yl, benzimidazol-2-yl, pyrimidin-2-yl and 2-pyridyl, or said heterocyclic residue having 1 to 3 substituents selected from $C_1$–$C_4$ alkyl, phenyl, $C_1$–$C_4$ alkoxy, nitro and halogen.

3. A process as defined in claim 2 in which $R^3$ in the compound of the formula (VII) is phenyl or phenyl having 1 to 3 substituents on the phenyl ring selected from the group consisting of $C_1$–$C_4$ alkyl, F, Cl, Br, I, $C_1$–$C_4$ alkoxy and nitro.

4. A process as defined in any one of claims 1, 2 and 3 in which about 1 to about 5 moles of the compound of the formula (VII) is used per mole of the compound of the formula (VI).

5. A process as defined in one of claims 1, 2 and 3 in which the reaction is conducted at a temperature ranging from $-20°$ C. to the the temperature at which the solvent used is refluxed.

6. A process as defined in claim 1 in which the organic solvent is at least one selected from the group consisting of acetone, methyl ethyl ketone, diethyl ketone, methyl isobutyl ketone, methyl formate, ethyl formate, propyl formate, methyl acetate, ethyl acetate, propyl acetate, methyl propionate, ethyl propionate, benzene, toluene, xylene, dichloromethane, dibromomethane, chloroform, bromoform, carbon tetrachloride, dichloroethane, dibromoethane, trichloroethane, diethyl ether, dipropyl ether, dibutyl ether, tetrahydrofuran, dioxane, nitromethane, nitroethane, nitropropane, acetonitrile, propionitrile, butyronitrile, valeronitrile, methanol, ethanol, propanol, isopropanol and butanol.

* * * * *